United States Patent [19]
Tang et al.

[11] Patent Number: 6,113,858
[45] Date of Patent: Sep. 5, 2000

[54] MONITOR WITH IN-SITU OPTICAL PROBE FOR CONTINUOUS CONCENTRATION MEASUREMENTS

[76] Inventors: Ruey-Long Tang, 2841 Villa Alta Pl., Hacienda Heights; Winston Z. Ho, 14541 Langhill Dr., Hacienda Hts., both of Calif. 91745

[21] Appl. No.: 09/012,972

[22] Filed: Jan. 26, 1998

[51] Int. Cl.[7] .......................... G01N 21/75; G01N 21/77; G01N 21/80
[52] U.S. Cl. ..................................... 422/82.09; 422/82.05; 422/66; 436/44; 436/79; 436/125; 436/163; 436/169
[58] Field of Search .............................. 422/82.09, 82.05, 422/66; 436/44, 79, 125, 163, 169

[56] References Cited

U.S. PATENT DOCUMENTS

| | | |
|---|---|---|
| 5,004,696 | 4/1991 | Clickenbeard . |
| 5,648,047 | 7/1997 | Kardish et al. . |
| 5,925,572 | 7/1999 | Byrne et al. . |

*Primary Examiner*—Jeffrey Snay
*Assistant Examiner*—Jennifer C. McNeil
*Attorney, Agent, or Firm*—Philip K. Yu

[57] ABSTRACT

An on-site monitor is disclosed for providing automatic measurements of chemical concentrations in a liquid or gaseous environment. The opto-electronic monitor has an extended probe, which can be inserted into the liquid or to be in contact with the ambiance, comprising a indicator chamber for continuously supplying fresh indicator material, a light source, and a detector. The light source and the detector are either embodied outside of liquid or into the extended plastic probe inside the liquid. A delivery unit, which is activated by a timer, delivers a small amount of indicator material into the liquid or a sampling cavity. The indicator material reacts with the ions in the liquid automatically. The light source has a wavelength which matches with the indicator's absorption wavelength and the detector measures the transmission (or reflection) through the indicator material or solution. The optical signal is converted into an electrical signal, calibrated with a known standard, and then displayed on an LED digital meter. The invention has the advantage of automatically and continuously measuring the chemicals on-site with self-powered, low maintenance, and simple operation.

21 Claims, 9 Drawing Sheets

MONITOR WITH IN-SITU OPTICAL PROBE FOR CONTINUOUS CONCENTRATION MEASUREMENTS

BACKGROUND OF THE INVENTION

1. Field of the Invention

The present invention relates to opto-electronic monitors for monitoring the quality of a liquid in a pool, a spa, a fish tank, a water reservoir, or a water flow system, and more specifically relates to monitors which can automatically measure various concentrations in the liquid and display their concentration on a low-maintenance and continuous basis.

2. Background of the Invention

In hot summer days, dipping into a swimming pool or a spa is one of the greatest enjoyment in life. Swimming is also known as one of the best exercises in the U.S., where there is a very large number of private swimming pools and spas in American families, schools and public facilities. However, what has been grossly overlooked by the millions of pool users is that no one seems to be able to obtain an accurate and up-to-date reading on the quality and sanitary condition of the water in the pool. While supposedly the water is periodically tested by the pool crew, the quality can drastically deteriorate in a very short time due to contamination.

The pool industry has not responded to this concern very well. In fact, the potential health risk has largely been overlooked and ignored. If anything, it would be quite comforting for pool users to know the quality of the water just before they dive in all the time. So far, pool users have mainly relied on the diligence of the pool crew for their own health risk, as they have no other way of ascertaining the quality of the pool. Or, the more naive ones have found comfort by relying on the fact that there are already people in the pool and they seem to be doing just fine.

Unbeknownst to the population, a pool may have bacteria and algae if not properly and regularly treated with chemicals or additives. Prolonged exposure to these harmful elements will adversely affect the eyes, skin, hair and eventually the overall well-being of every pool user. To ensure the overall well-being of the user population, it would be desirable to have an on-site pool water monitoring device for accurately determining the concentration of the main contaminants, namely acidity, chlorine, alkalinity, calcium, magnesium, iron, and bromide, in the pool water.

There are generally three types of water monitoring devices in the pool industry. One of them is the chemical-based indicators, in either solution or dip-strip substrate form, which are widely used by private pool owners due to their low cost. However, this type of indicators, which is based on visual observation of color comparison using standard solutions, is inconvenient and often gives inaccurate results. Most pool owners use this type of monitors to check pool water quality once every week. To ensure excellent water quality on a constant basis, pool owners or users will have to check more frequently or around the clock.

The second type is a hand-held electrode-based monitor which uses un-equilibrium electronic charge transfer or electrochemical potential between the pool water and the electrolytic cell through a membrane. Again, this type of indicator has proven fundamentally unsuitable for continuous on-site measurement. The third type of monitors is an optical-based monitor as described in an U.S. Patent issued to Saaski, et. al., U.S. Pat. No. 5,039,492. This type of monitors employs an optical method based on the resulting color change of an indicator substrate to measure the pH and gas concentrations in sampling blood. Although this method also is derived from the same general optical principle, it is intended for only one time use and not for continuous use in a pool or spa environment.

Therefore, it would be desirable to have an on-site water monitor for continuously monitoring the quality of the pool water on a low-cost, low-maintenance basis.

SUMMARY OF THE INVENTION

One of the objects of the present invention is to provide a monitoring device for automatically measuring the pH, chlorine, alkalinity, metals, and/or bromide concentrations in aqueous solution.

It is also an object of the present invention to provide a battery, or solar, operated monitoring device which is of a simple, inexpensive construction and requires minimal maintenance for on-site monitoring.

It is yet another object of the present invention to provide an in-situ extended optical probe for continuous monitoring, where the probe includes a continuous supply of fresh indicator material.

It is also an object of the present invention to provide an automatic pump with a tube extended into the liquid for continuously supplying samples into the sample cavity for probing.

A further object of the present invention is to provide a monitoring device which continuously displays the chemical concentration on a permanent basis.

Another object of the present invention is to provide a monitoring device which can calculate the amount of treated chemical, or balancing particles, required to be added to the pool on a permanent basis.

The foregoing objects can be accomplished by constructing a monitoring device comprising an indicator solution or an indicator patch, a light source, a detectors, a power supply, signal processing electronics and display electronics. The indicator solution or patch may be set up to contain separate indicator solutions or patches which are available for separate testing of any predetermined particles in the liquid under test.

The light source, such as a light emission diode (LED) with a wavelength matching the indicator's absorption wavelength and the detector, such as a photodiode, can be placed either above and away from the pool water or inserted into the pool water. A delivery unit, which is activated and controlled by a timer, delivers a small amount of the fresh indicator solution or unrolls a fresh indicator patch which is attached onto an indicator supply strip into the sampling cavity upon contact. The indicator material reacts with the ions in the pool water automatically.

Upon reaction, the color of indicator solution is read by the light source and the optical detector. In the case of indicator patches, the reacted patch can be forward rolled to the sensor position and read by the sensor. The detector measures the intensity of the transmitted light or the reflective light through the indicator patch or testing solution in the sampling cavity. The optical signal is converted into an electrical signal, calibrated with a known standard, and then digitally displayed on an LED panel. Based on the measured concentration and the quantity of the pool water, the microprocessor can further calculate the amount of treated chemical, or balancing particles, needed to be added into the pool to ensure water quality.

The present invention has the advantage of automatically measuring the chemicals on-site with a self-powered, low-maintenance, and simple operation. As will be appreciated by those skilled in the art, the benefit of the present invention to pool users' overall well-being is potentially immense. Further, as it will become apparent to those skilled in the art, the teaching of the present invention can be applied to monitoring devices for monitoring the quality of a variety of liquid or air samples.

DETAILED DESCRIPTION OF THE PREFERRED EMBODIMENTS

Figure 1:
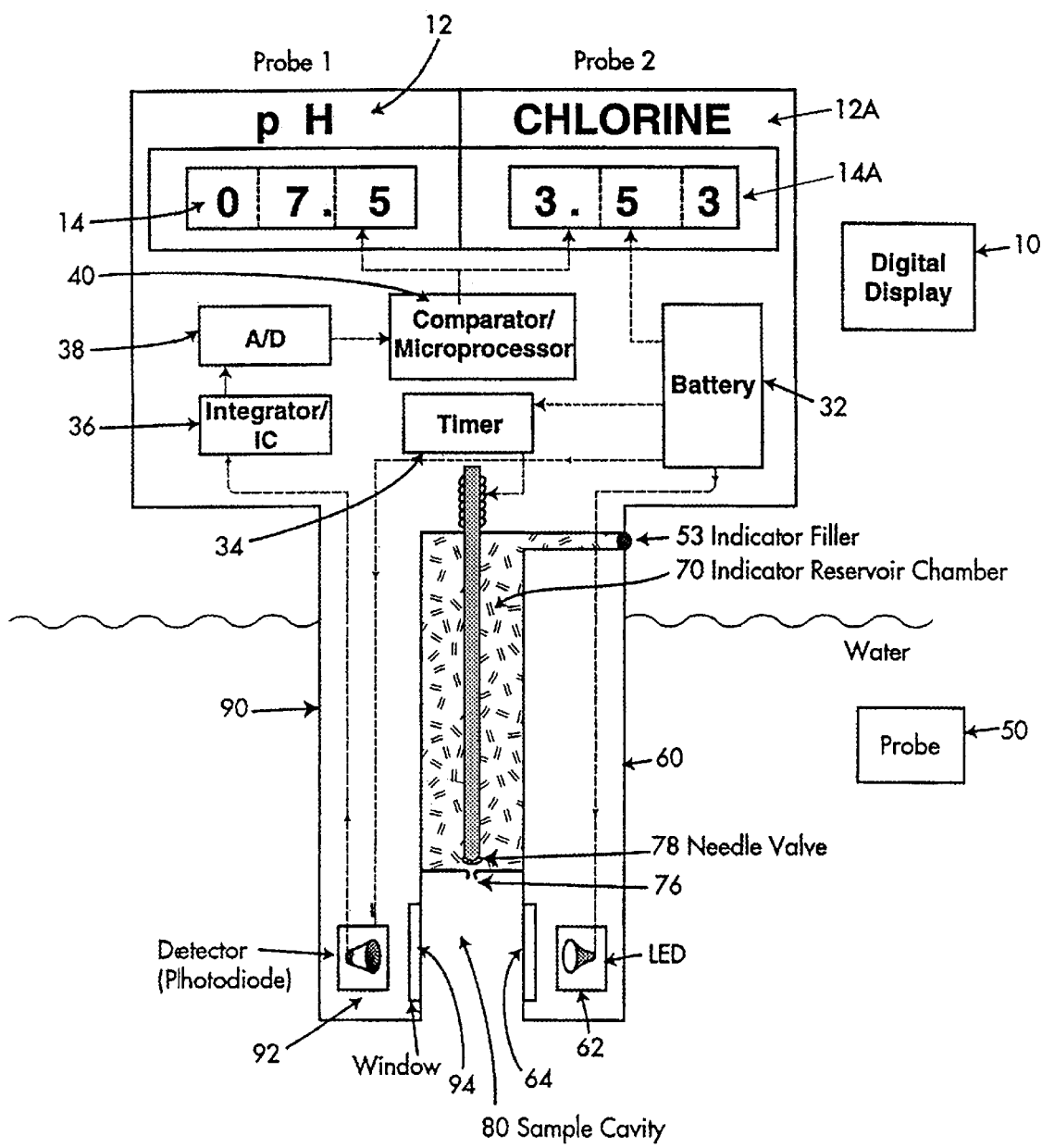
FIG. 1 is an exemplary embodiment of the present invention with its probe linked to a multiple digital display meter.
Figure 2:
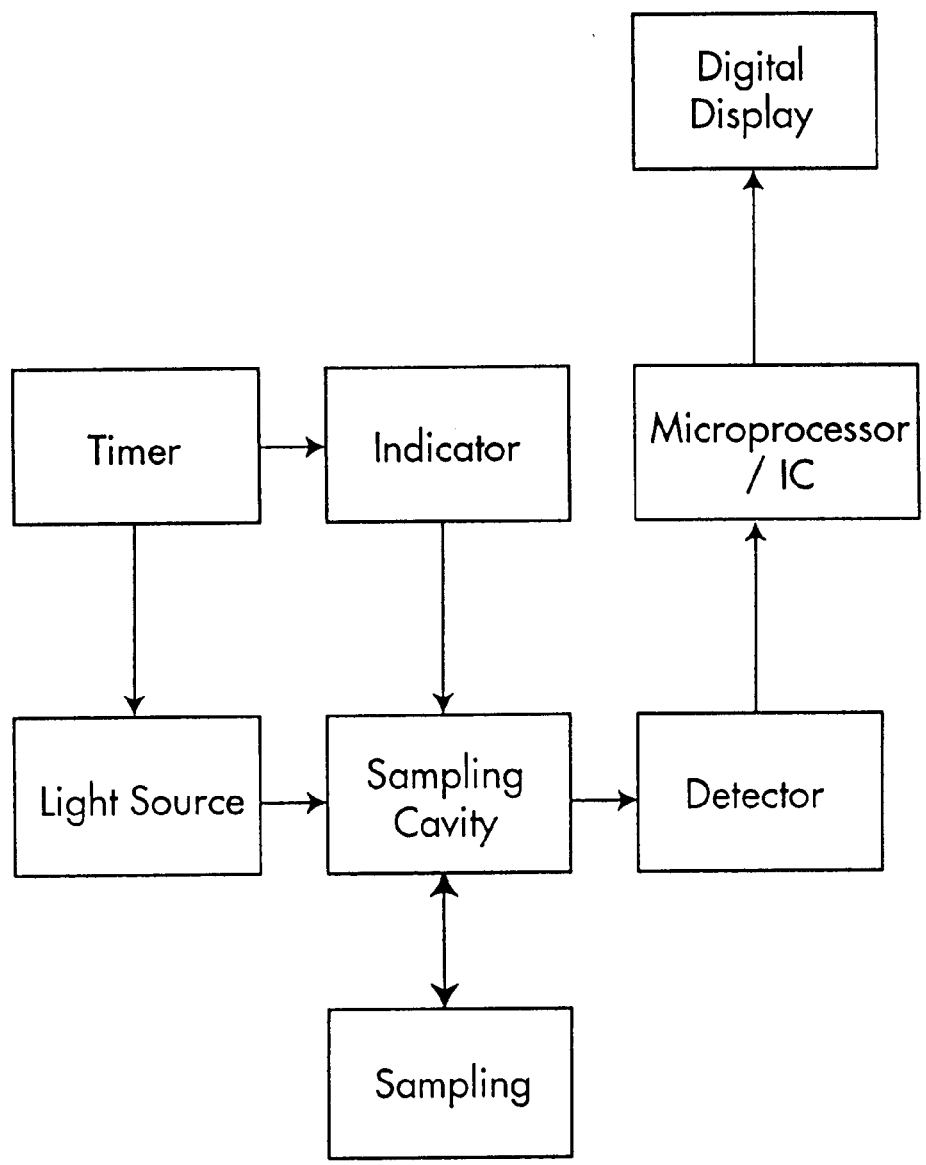
FIG. 2 shows a simplified system diagram of the present invention.

FIG. 1 shows one exemplary embodiment of a monitoring device for monitoring the quality of any liquid or water in pools, fish tanks, spas, or water flow systems in accordance with the present invention. FIG. 2 illustrates the system diagram in accordance with its continuous monitoring principle. As can be understood by those skilled in the art, the device is capable of continuously supplying fresh indicators, measuring the optical characteristics of the indicator after its reaction with the ions in the liquid, and displaying the measurement on a digital meter. The light source and detector can be implemented either inside the liquid or outside the liquid to be tested.

It should be noted that the present invention is described in terms of commonly known components and elements, which are the means generally used by those skilled in the art in communicating with each other. Based on the disclosure of the present invention, those skilled in the art can readily implement the present invention, without undue experimentation, for a variety of applications. For example, it should be well understood by those skilled in the art that the application of the present invention is not limited to monitoring water quality in the pool. In fact, with the teaching of the present invention, those skilled in the art can readily implement various monitoring devices for various kinds of fluids, liquids or even gaseous environment. However, the description of the present application for use with the pool water is intended to illustrate the present invention without unnecessarily obscuring it.

As in FIG. 1, the monitoring device may be implemented by using a plastic molded display case 10 and a plastic molded probe case 50. The display case 10 may be implemented to include all the signal processing electronics and digital display elements. The preferably elongated square probe case 10 should be long enough to be immersed into the water for in-situ monitoring. The probe 10 has an indicator reservoir chamber 70 and a sampling cavity 80, which are "sandwiched" between a light source chamber 60 and a detector chamber 90. The indicator reservoir chamber 70 holds a large quantity of an indicator material either in a solution form 71, in a solid form 81 (FIG. 4) or in a patch form 88 (FIG. 5), as will be described in connection with FIGS. 3, 4 and 8, respectively.

Figure 3:
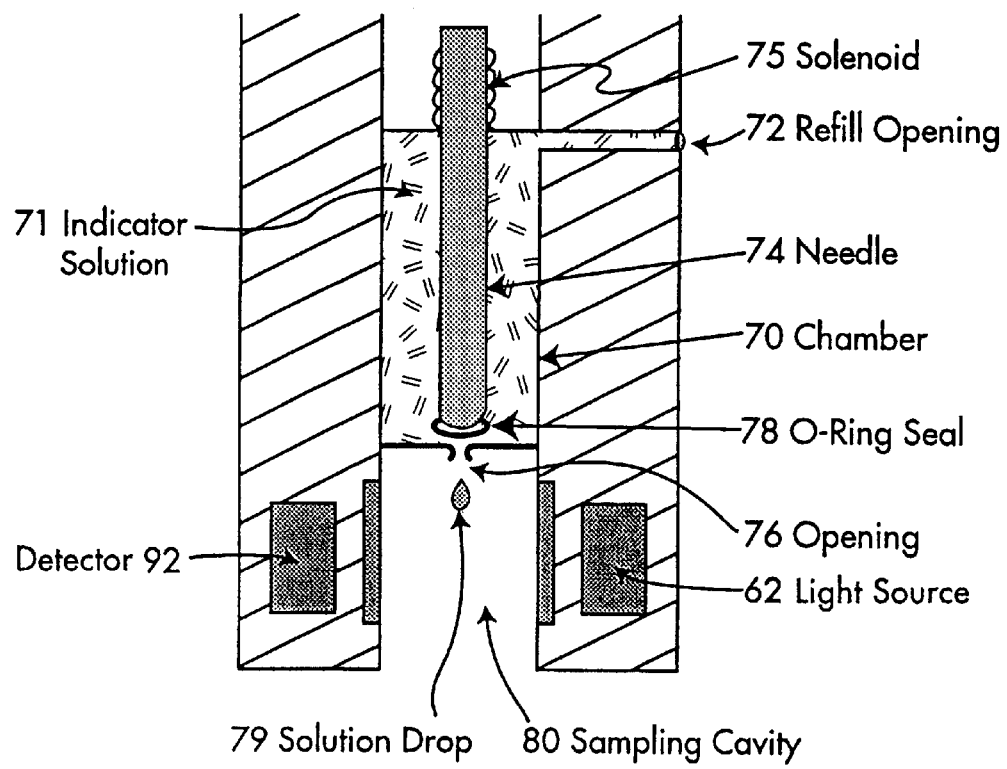
FIG. 3 shows a view of an indicator chamber with continuous fresh indicator supply.

FIG. 3 shows one embodiment of an indicator chamber 70 filled with an indicator solution 71. The solution is refillable through a small opening 72. At the bottom of the chamber 70, a valve mechanism is activated by a timer 34 (FIG. 1) to deliver one or a few drops of the indicator solution at a certain set time. For example, the valve mechanism can include a small needle 74, an opening 76 and an O-ring seal 78 to prevent leakage of the indicator solution to the pool water. The needle 74 is activated by an electronic solenoid 75, which is controlled by the timer 34. Whenever the valve mechanism opens up, a pre-set amount of the indicator solution 71 is delivered into a sampling cavity 80. The drop of indicator reacts with the chemicals in the water and shows nearly instantly a color change. Since each measurement requires only one drop 79 of the indicator solution, the refilling process will not be needed for a long time, which achieves the object of a low-maintenance operation.

Figure 4:
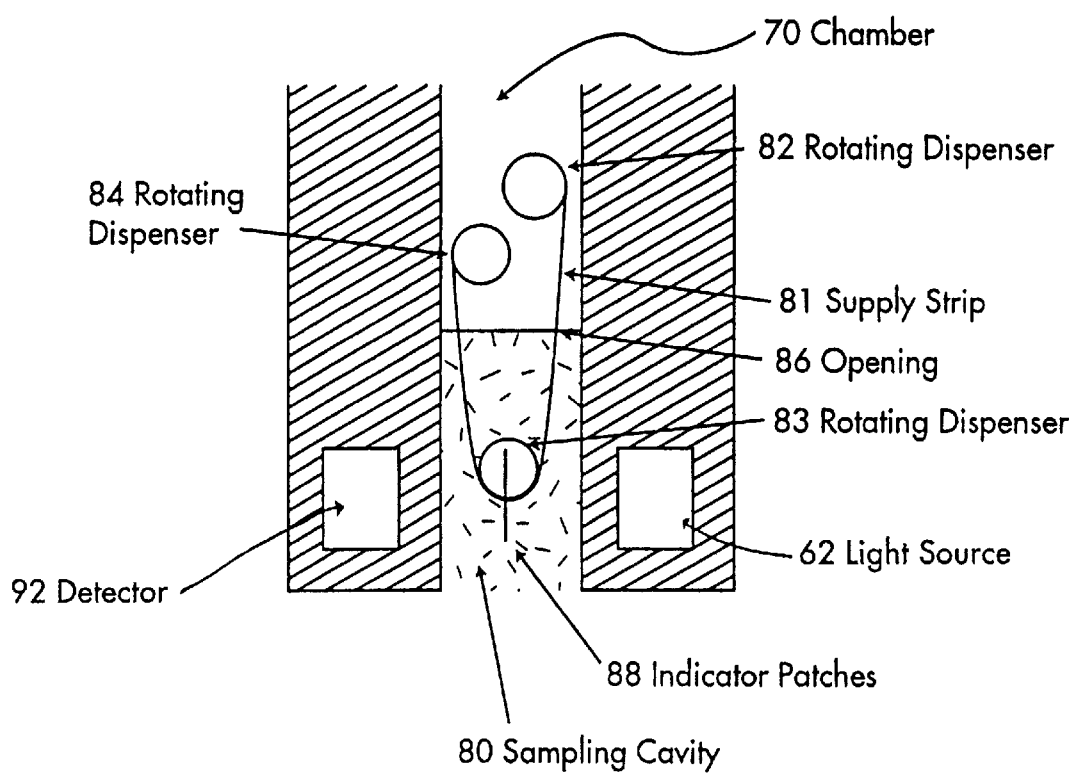
FIG. 4 displays a front view of a roll of an indicator supply strip inside the indicator chamber.

FIG. 4 displays another embodiment of the indicator chamber 70 using a solid form indicator material. A roll of the indicator supply strip 81 is mounted on a rotating dispenser 82, 83, 84, to continuously supply fresh indicator material. A large amount of indicator patches 88, impregnated with a solid indicator, may be attached onto the indicator supply strip 81. Because the indicator patch 88 is made of a porous substrate, such as membrane, the pool water can easily diffuse into the pores and react with indicator material. The strip 81, which may be made of optically clear material, transports the indicator patch from the indicator chamber 70 through an opening 86 into the sampling cavity 80, and then back into the indicator chamber 70 for storage. The rotating dispenser 82, 83, 84, which may be implemented with electro-mechanical gears, is activated by the timer 34 at a certain set time.

As shown in FIG. 4, the sampling cavity 80, where the indicator reacts with the ions in the water, may be located underneath the indicator chamber 70 and between the light source 62 and the detector 92. The sampling cavity 80 is exposed to the pool water for such reaction to take place. Therefore, the indicator material is automatically exposed to the pool water as soon as it is delivered into the sampling cavity 80.

The sampling cavity 80 can be five-side physically confined by the walls of the indicator chamber, light source chamber, and detector chamber, while the bottom side of the sampling cavity 80 is open to the pool water. The fresh, or unused, indicator, either in solution form 79 or in solid substrate form 88, changes color after it reacts with the ions in the pool water. The reaction process may take a few seconds for the indicator to homogeneously admix with the pool water. Those skilled in the art can readily take advantage of a variety of indicators or organic dyes, which have been developed in the industry and which are sensitive to the concentration of certain chemical ions.

Figure 5:
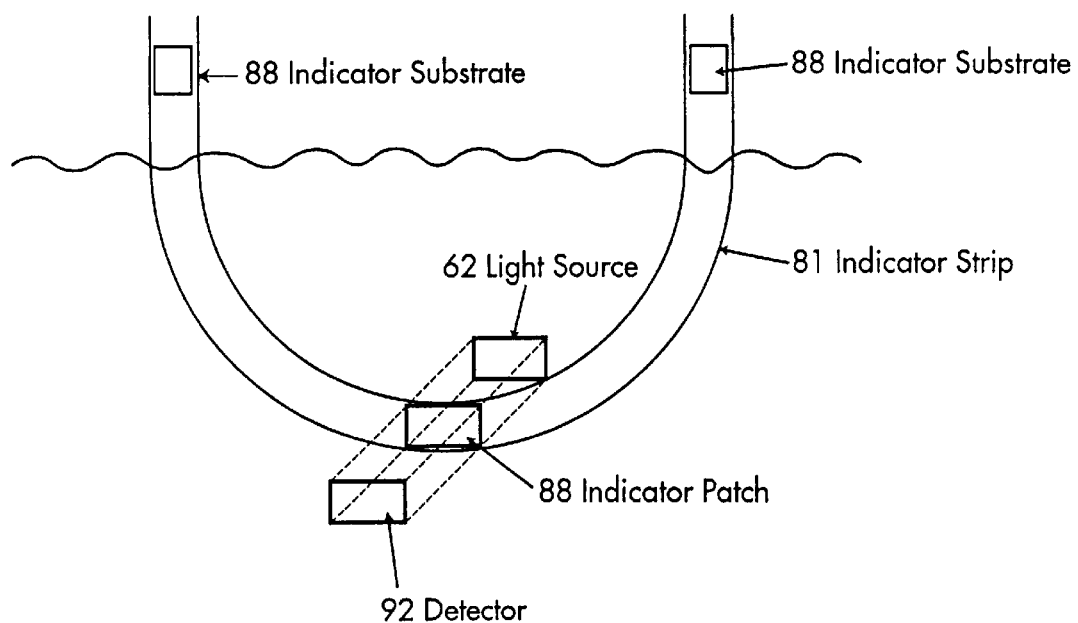
FIG. 5 shows an angled view of an indicator strip disposed in the optical path between a light source and a detector in transmission mode.

FIG. 5 is an angled view of the indicator supply strip 81 with an indicator patch 88 rolled into the water, or sample cavity, and disposed exactly in the optical beam path between the light source 62 and the detector 92. When the timer 34 expires at its preset interval, a fresh indicator patch 88 is rolled into the sampling cavity 80. When the pool of water disperses into the patch substrate 88, the indicator material interacts with the chemicals in the water. As can be appreciated by those skilled in the art, a roll of strip 81 with a large amount of indicator patches can be used for many measurements. The indicator strip 81 with indicator patches 88 can be replaced when all of the substrates are used up.

Figure 6:
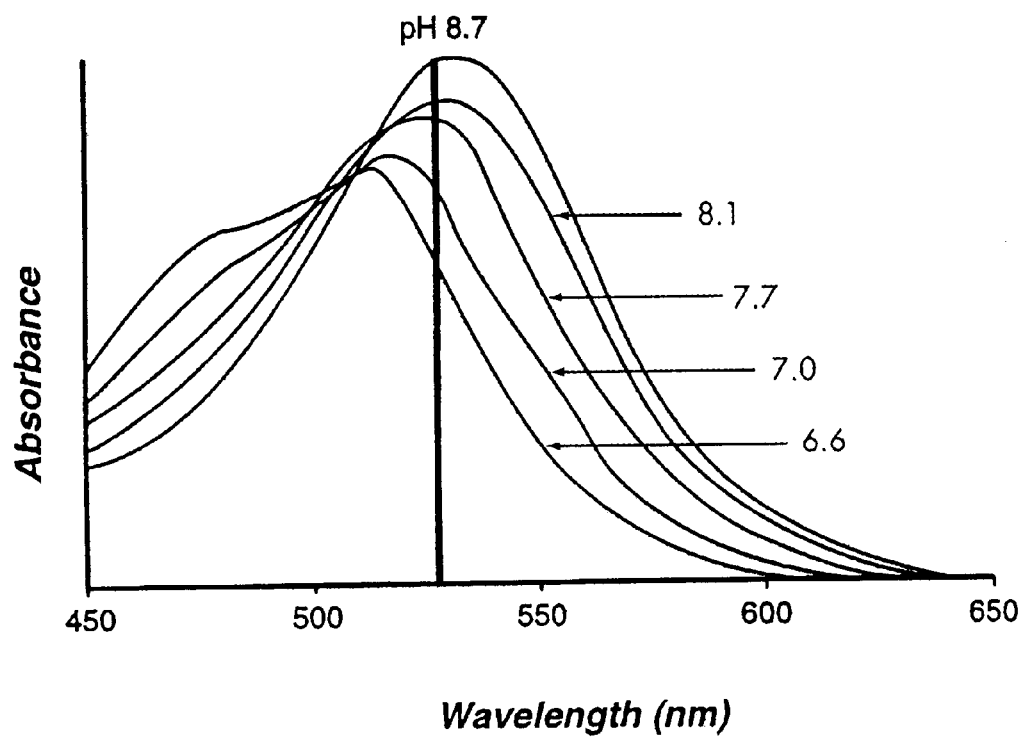
FIG. 6 shows an example of the indicator's optical characteristics.

FIG. 6 shows a pH-dependent absorption spectra of SNAFL calcine indicator. (SNAFL is a trademark of Molecular Probe Inc.) The absorption or transmission intensity of the indicator at a selected wavelength is directly related to the ion concentration in the water. The indicator material can be easily incorporated into the transparent polymeric membrane or substrates. DPD, N, N-diethyl-p=phenylenediamine, is a USEPA-accepted method for detecting chlorine for water and wastewater. Based on the color intensity at red region, the method can accurately detect chlorine from 0 to 500 mg/l. As those skilled in the art can readily appreciate, there are quite a few indicators available in the industry, which are sensitive to the variety of chemicals in the water, or liquid under test.

Figure 7:
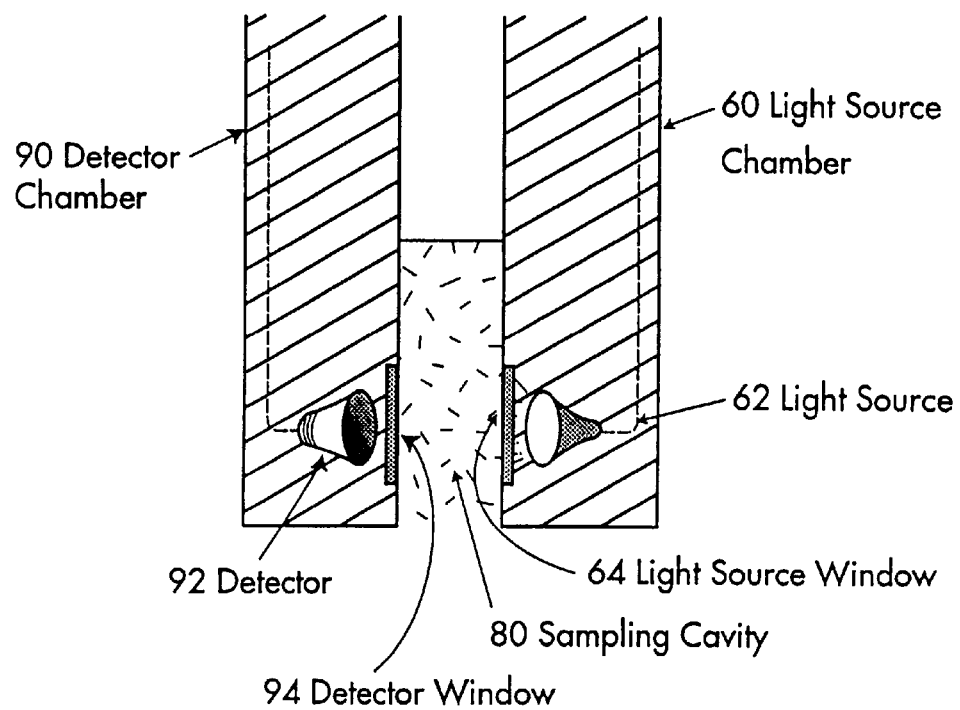
FIG. 7 is a partial view of a sampling cavity disposed between the light source and the detector.

FIG. 7 shows a light source 62 and a detector 92 in the light source chamber 60 and detector chamber 90, respectively. Both are disposed inside the elongated probe case as two arms with the sampling cavity 80 in-between. The light source 62, such as a light emission diode (LED), with an optimum wavelength for characterizing the indicator's absorption property, can be used. Various wavelength LEDs are also available for selection by those skilled in the art in their particular implementation. Light passes through a light source window 64, a sampling cavity 80, a detector window 94, and a detector 92 to form an optical path. If the light source and detector chambers are constructed with transparent plastic cases, the two windows 64 and 94 may not be necessary. The photodetector 92, such as a photodiode, is sensitive within visible range and can be used for optical intensity measurement. Both the LED and photodiode are wired to a DC battery power supply. Note that the power supply can also be implemented using solar cells so as to eliminate the need to replace batteries regularly.

Figure 8:
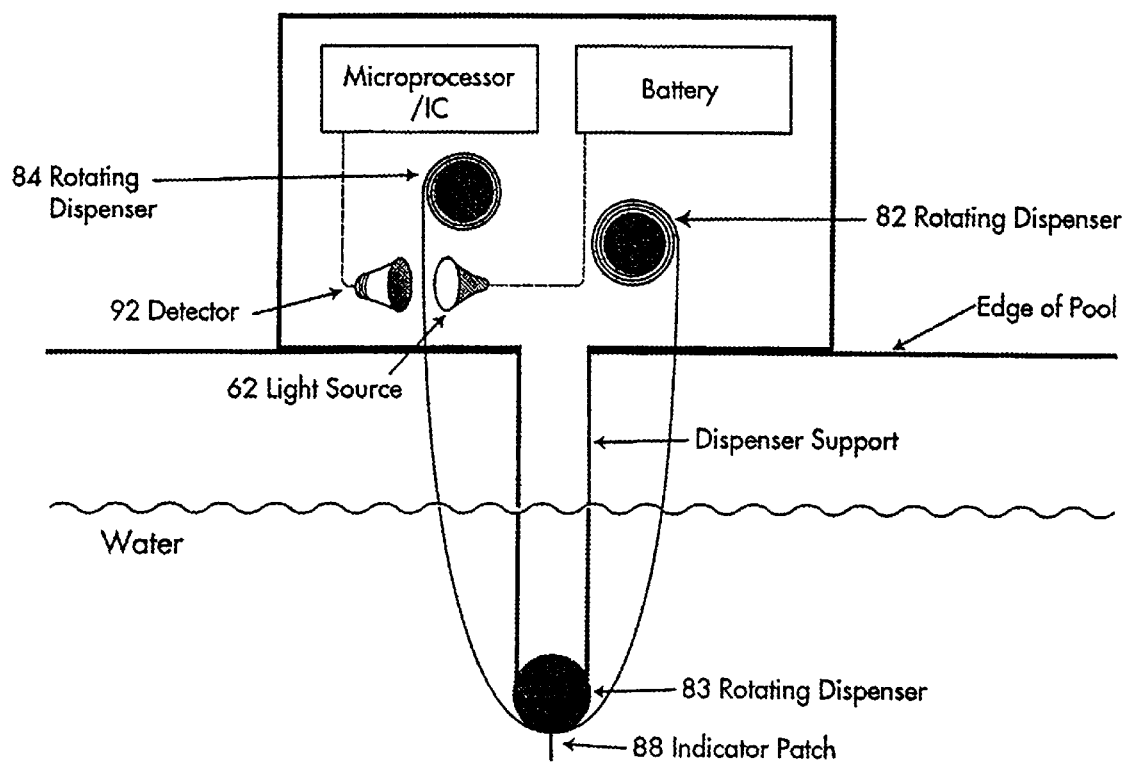
FIG. 8 displays a front view of a light source and a detector embodied outside and way from the water, and a roll of an indicator supply strip.

FIG. 8 displays another embodiment of a roll of an indicator supply strip, similar to FIG. 4, but with the light source 62 and detector 92 away from the water. The roll of the indicator supply strip 81 is mounted on a rotating dispenser 82, 83, 84, to continuously supply fresh indicator patch 88 into the pool water. The reacted indicator patch 88 is then rotated to a position located between the light source and the detector. The light source 62 and the detector 92 can be installed as part of the digital display 10 package and measure the color change of the indicator patch 88. This configuration can avoid the possible electrical contact with water as shown in FIG. 4.

With respect to FIG. 8, another embodiment can be implemented, where the light source 62 and detector 92 are each connected by individual optical fibers, which extend into the water. At the other end of the fibers, the fibers are positioned such that the light source fiber can pass its light through the indicator patch 88 to be sensed by a sensor at the other end of the detector fiber. This embodiment has the advantage of using optical fibers to help the light source 62 and detector 92 reach further, for example, into a deeper pool. Also, if the pool edge is much higher than the water level, this embodiment can use its fibers to reach the water without having to place the rest of the electronics near the water. Further, if the water is level is subject to change, e.g. in a reservoir, the extended reach can prevent the main body of the monitoring device from being submerged in the water by allowing the device to be placed afar.

Figure 9:
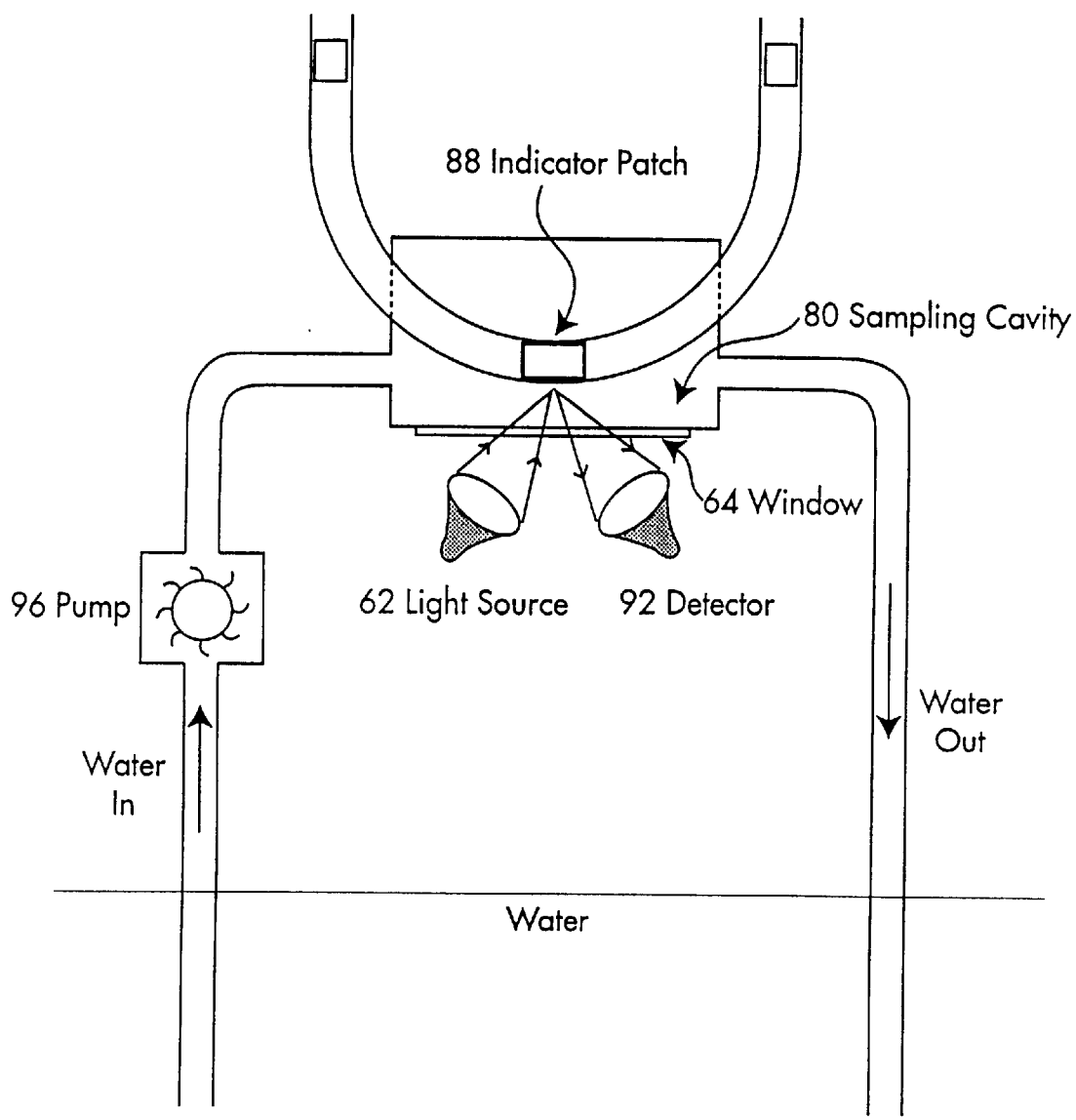
FIG. 9 displays a monitoring device using a pump to pump the water through a tube into the sample cavity which is located outside the water. The optical reading mechanism shown is based on the reflective mode.

FIG. 9 is another configuration which shows the device with an additional pump 96 which can pump the water sample from the pool into the sampling cavity 80 which is located outside and away from the water. The pump will be activated by the timer 34 and pump water sample into the sampling cavity. The water sample reacts with the newly supplied indicator materials, either in solution form or in solid substrate form, in the sampling cavity. The color of the indicator material will change according to the chemical concentration in the water sample. FIG. 9 shows the optical measurement mechanism based on the reflective mode, in which the light source 62 and detector 92 are located on the same side of the sample, and the detector measures the light intensity reflected from the sample/indicator.

Reference is back to FIG. 2, where the basic principle of the operation is described. The user pre-sets the time and frequency or time interval for chemical testing on a timer 34. The timer initiates the operation by first delivering the indicator material into the sampling cavity which is either open to the liquid to be monitored, or can access new samples, then activating the light source to illuminate the liquid/indicator solution (or substrate), and finally measuring the transmissive, or reflective intensity with a detector.

It should be understood by those skilled in the art that the present invention can be readily applied to a method and apparatus for monitoring the quality of air or gaseous samples. By allowing the testing material to be in contact and react with the samples from the environment, a light source can be used to obtain the necessary information based on the color change of the testing material. For example, the indicator solution can be sprayed, using an atomizer, into the sampling cavity for the light to detect any color change. As such, the quality of the environment can be monitored continuously.

After the detector detects the transmitted light, the electrical signal is sent to the display case 10 for signal integration, amplification, and digitization, as can be readily understood and implemented by those skilled in the art. The electronic display case 10 may comprise common electronic components such as an integrator/amplifier 36, an analog-to-digital converter (A/D) 38, a comparator/microprocessor 40, a digital display meter 14 and 14A, a timer 34, and a battery-operated power supply 32, or solar cells. A series of known values corresponding to the known chemical concentrations will be stored in the comparator for calibration. Based on the detection value, the microprocessor can determine if the end of indicator is reached or the indicator material is running out. A red LED can inform the user that fresh indicator material is needed in the indicator chamber. Those skilled in the art can further design equivalents for the users to input the quantity of the liquid or fluid to be monitored in a unit of ×1000 gallons. This microprocessor 40, based on this pre-set quantity and measured pH, or bromide values, can calculate the required treated chemicals for the liquid. An eight-segment digital red LED may be used to display the reading of the measurement. The meters 14 or 14A will update the concentration value whenever a new reading has been initiated. The timer 34 which controls and initiates the device operation can be preset for any period of time interval for testing.

The information thus obtained can also help determine the amount of additional chemicals needed to balance the quality of the water, liquid or environment. Using pre-set algorithm and calculation routine, the amount of balancing particles needed to maintain, say, the pool water quality can be displayed for the user. Or, in the case of a monitoring device for the air quality in a room, the information can be used to activate air freshener agents to balance the air quality automatically. As can be appreciated by those skilled in the art, the continuous and low-maintenance operation of the present invention can lead to a truly "intelligent" monitor for a variety of applications.

Once the quality of the liquid can be detected, the present invention can also be extended to include a wireline or wireless transmitter to transmit the detection result to a remote data processing center. This is particularly useful in monitoring the quality of liquids or fluids located at different physical locations, such as at different points of a river, stream or aqueduct. With this methodology, the quality of a river or several of them can be monitored by a central location in a low power and low maintenance way.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A monitor for continuously monitoring the quality of a liquid by monitoring the concentration of a predetermined particle in the liquid, comprising:
   a probe being immersed into the liquid, the probe having an open sampling cavity in contact with the liquid;
   an indicator coupled to the probe for holding a predetermined amount of at least one predetermined indicator solution, the indicator solution capable of being refilled such that the indicator is continuously supplied with the indicator solution, the indicator solution generating a predetermined color when the indicator solution admixes with the predetermined particle in the liquid;
   a delivery unit coupled to the indicator for dispensing a predetermined amount of said at least one indicator solution to react, in the sampling cavity, with the liquid in a predetermined time interval;
   a light source disposed within the probe for emitting light through the sampling cavity, the light having a wavelength which is color-sensitive to the indicator solution upon reaction with the liquid;
   an optical detector coupled to the light source for detecting the light after the light is applied to the sampling cavity to detect if the light has changed to a predetermined color, and
   an optical signal processing unit coupled to the optical detector for reading the light and generating concentration information based on the predetermined color of the light, the optical signal processing reading the light based on the predetermined time interval such that the presence of the predetermined particle in the liquid is continuously monitored.

2. A monitor according to claim 1, wherein a presence of said one particle represents a presence of one of the following in the liquid: acidity, chlorine, alkalinity, calcium, magnesium, iron, and bromide.

3. A monitor according to claim 2, in which said signal processing unit further comprises a calculating unit for calculating the amount of at least one balancing particle required to add to the liquid in order to achieve a desired quality, wherein said amount of said at least one balancing particle is calculated based on the quantity of said liquid and the measured quality of the liquid determined by the optical signal processing unit.

4. A monitor according to claim 1, in which said signal processing unit further comprises a calculating unit for calculating the amount of at least one balancing particle required to add to the liquid in order to achieve a desired quality, wherein said amount of said at least one balancing particle is calculated based on the quantity of said liquid and the measured quality of the liquid determined by the optical signal processing unit.

5. A monitor for continuous monitoring a presence of at least one predetermined particle in a liquid, comprising:
   a probe being immersed into the liquid, the probe having a sampling cavity in contact with the liquid;
   an indicator disposed within the probe for holding a refillable roll of indicator strips comprising a plurality of indicator substrates impregnated with at least one solid indicator material, each indicator substrate capable of being transported to the sampling cavity, the indicator substrate generating a predetermined color when the indicator substrate admixes with said at least one particle in the liquid;
   a delivery unit coupled to the indicator for transporting a predetermined amount of the indicator substrate into the sampling cavity to react with the liquid in a predetermined time interval;
   a light source coupled to the probe for emitting a light into the sampling cavity, the light having a wavelength which is color-sensitive to the indicator substrate upon reaction with said at least one particle in the liquid;
   an optical detector coupled to the light source for detecting if the light has changed to a predetermined color;
   an optical signal processing unit coupled to the optical detector for reading the light and generating concentration information based on the predetermined color of the light having been applied to the indicator substrate, the optical signal processing reading the light based on the predetermined time interval such that the liquid is continuously monitored.

6. A monitor according to claim 5, wherein the at least one particle is indicative of the presence of at least one of the following in the liquid: acidity, chlorine, alkalinity, calcium, magnesium, iron, and bromide.

7. A monitor according to claim 5, in which said signal processing unit further comprises calculating unit for calculating the amount of at least one balancing particle required to add to the liquid in order to achieve a desired quality, said amount being calculated based on the predetermined quantity of the liquid and the measured chemical concentration.

8. A monitoring device for monitoring the quality of ambiance by monitoring the presence of at least one predetermined particle in the ambiance, comprising:
   a probe, the probe comprising an open sampling cavity in contact with the ambiance;
   an indicator coupled to said probe for storing a predetermined amount of indicator material;

a delivery unit coupled to said probe for dispensing, in a predetermined time period, said predetermined amount of said indicator material into said sampling cavity for reaction with the ambiance, said indicator material interacting with said at least one predetermined particle to result in a color change;

a light source coupled to said sampling cavity for emitting a light into said sampling cavity and to said now-reacted indicator material, said light having a predetermined wavelength which is sensitive to said color change of said indicator material;

an optical detector coupled to said sampling cavity for detecting said light after it is emitted through said sampling cavity to detect said color change;

an optical signal processor unit coupled to said optical detector for reading the light as detected by said optical detector upon a predetermined time interval, such that the quality of the ambiance is continuously monitored.

9. The monitor according to claim 8, wherein said indicator material comprises a roll of indicator patches installed with a rotating dispenser.

10. The monitor according to claim 9, wherein said indicator comprises an opening for refilling said indicator material.

11. The monitor according to claim 8, wherein said indicator material comprises a predetermined amount of indicator solution for periodic release into said sampling cavity for interacting with the ambiance.

12. The monitor according to claim 8, wherein said delivery unit comprises a needle, an electric solenoid, and an opening, said electric solenoid causing said needle to control the opening of said opening to said sampling cavity.

13. The monitor according to claim 8, wherein said indicator comprises an opening for refilling said indicator material.

14. The monitor according to claim 8, wherein the ambiance is either one of a liquid or a gaseous environment.

15. The monitor according to claim 8, wherein:

the indicator holds a refillable roll of indicator strips comprising a plurality of indicator substrates impregnated with at least one solid indicator material, each of the indicator substrate capable of being transported to the sampling cavity for reaction with the ambiance, the indicator substrate generating a predetermined color when the indicator substrate admixes with said at least one particle in the ambiance.

16. The monitor according to claim 8, wherein said signal processing unit further comprises calculating unit for calculating the amount of at least one balancing particles required to add to the ambiance in order to achieve a desired quality, said amount of at least one particle being calculated based on the predetermined quantity of the ambiance and the measured quality so determined.

17. A monitor according to claim 15, in which said signal processing unit further comprises calculating unit for calculating the amount of at least one balancing particles required to add to the ambiance in order to achieve a desired quality, said amount of at least one particle being calculated based on the predetermined quantity of the ambiance and the measured quality so determined.

18. A monitor for monitoring the concentration of a predetermined particle in an ambiance, comprising:

a probe being immersed in the ambiance, the probe comprising an open sampling cavity in contact with the ambiance;

a refillable indicator unit coupled to the sampling cavity, the indicator unit holding a predetermined amount of testing material, said testing material generating a predetermined color when the testing material admixes with the predetermined particle in the ambiance;

a delivery unit coupled to the refillable indicator unit, the delivery unit periodically supplying a predetermined amount of testing material to the open sampling cavity to react with particles in the ambiance;

a light source coupled to the probe, the light source emitting light into the sampling cavity, the light having a wavelength which is color-sensitive to the testing material after the testing material reacts with the predetermined particle in the ambiance;

an optical detector coupled to the light source for detecting any color change of the light after the light is applied to the sampling cavity;

a signal processing unit coupled to the optical detector, the signal processing unit reading the light and generating concentration information based on the color of the light emitted through the sampling cavity.

19. The monitor according to claim 18, wherein the testing material comprises a predetermined solution.

20. The monitor according to claim 19, wherein the testing material comprises a supply of solid indicator substrates impregnated with at least one solid indicator material.

21. The monitor according to claim 19, wherein the delivery unit further comprises an atomizer for spraying the predetermined solution to the sampling cavity.

* * * * *